United States Patent [19]

Miller

[11] 4,378,494
[45] Mar. 29, 1983

[54] APPARATUS AND METHOD FOR DETECTING DEFECTS IN GLASS BOTTLES USING EVENT PROXIMITY

[75] Inventor: John W. V. Miller, Toledo, Ohio
[73] Assignee: Owens-Illinois, Inc., Toledo, Ohio
[21] Appl. No.: 205,056
[22] Filed: Nov. 7, 1980
[51] Int. Cl.³ .......................................... G01N 21/90
[52] U.S. Cl. .............................. 250/223 B; 250/563; 356/237; 356/240; 358/106; 209/526
[58] Field of Search ..................... 250/223 B, 563, 572; 209/522, 524, 526, 529; 356/237, 239, 240; 358/106

[56] References Cited

U.S. PATENT DOCUMENTS

| | | | |
|---|---|---|---|
| 3,827,812 | 8/1974 | Heimann | 250/223 B X |
| 3,969,577 | 7/1976 | Lloyd et al. | 358/106 |
| 4,213,702 | 7/1980 | Bryant et al. | 250/223 B X |
| 4,292,672 | 9/1981 | Southgate | 358/106 X |

*Primary Examiner*—David C. Nelms
*Assistant Examiner*—Edward P. Westin
*Attorney, Agent, or Firm*—G. T. Welch; D. H. Wilson; M. E. Click

[57] ABSTRACT

An apparatus and a method for identifying defects in objects, such as glass bottles, utilizing data signals generated from a photodiode camera and light source. Event signals are generated when the magnitudes of adjacent data signals differ by an amount which exceeds a threshold level. Signals are also generated to identify the location of each event signal with respect to a corresponding photodiode and to identify during which vertical sweep of the object the event signal was generated to associate the event signal with a point on the object. The event signals are processed to identify defects. Events in proximity in the same sweep are identified as a string. Event magnitudes and totals in a string are compared with predetermined values to identify defects. Strings in proximity are identified as a blob. Event magnitudes and totals and blob width are compared with predetermined values to identify defects.

32 Claims, 2 Drawing Figures

APPARATUS AND METHOD FOR DETECTING DEFECTS IN GLASS BOTTLES USING EVENT PROXIMITY

BACKGROUND OF THE INVENTION

1. Field of the Invention

The present invention relates in general to sidewall inspection devices for containers and in particular to a method and apparatus for detecting defects in glass bottles using event proximity.

2. Description of the Prior Art

The use of optical scanning devices for inspecting the sidewalls of containers is well known. Numerous devices, such as those shown in U.S. Pat. Nos. 3,708,680 and 3,716,136, have circuitry including means for receiving and interpreting light passed through or directed onto an item under inspection. Such devices incorporate either a visual display for comparison of the item or employ a device capable of producing a resistance proportional to the intensity of light directed thereon. Whether the output of such a device is visual or electrical in nature, it is eventually compared against a model to determine if the item under inspection is suitable as to size and construction and is without flaws, cracks, or foreign objects. Such devices are each intended to provide an automated inspection means for checking, as in a moving column of bottles, single or multiple objects in that moving column.

U.S. Pat. No. 3,877,821 discloses an apparatus having a scanning array that is serially interrogated to generate a train of pulses having amplitudes representing the light transmitted through an object under inspection. Adjacent pulses are compared to generate pulses having amplitudes which represent the difference in pulse amplitudes. The different pulses can be utilized to indicate a defect in the object being inspected. U.S. Pat. No. 3,942,001 discloses an apparatus for detecting the presence of extraneous matter or cracks in translucent containers. A spot beam of light is projected through the container to generate an inspection signal which is compared with an acceptance signal. The acceptance signal amplitude is varied in accordance with the position of the spot beam with respect to the container.

SUMMARY OF THE INVENTION

The present invention concerns an apparatus and method for extracting data from a scan of a glass container and utilizing the extracted data to determine the physical size and intensity of localized defects to ascertain the acceptability of the container. A photodiode array and light source are utilized to generate signals representing the amount of light received from points on the container. Event signals are generated when the magnitudes of adjacent diode signals are different by an amount which exceeds a threshold level. The event signal magnitude and position are stored in an inspection device interface and transferred to either a first or second control unit, both of which are responsive to the event signals for determining whether to generate a reject signal.

A master control means alternatively connects one of the first and second control units to the interface, whereby the connected control unit receives the event signals from the interface while the other control unit determines whether to generate a reject signal by processing the event signals of a preceding bottle. In making this determination, each event along a vertical sweep is checked to see if it can be linked to a preceding event by not exceeding a user-specified separation between the associated points on the container. A string is formed when two or more events are in proximity to each other. The apparatus checks for excess string magnitude as one basis for bottle rejection. If a bottle is not rejected on a string, the strings are checked to see if they form a blob. A blob is a plurality of strings in proximity to each other. If there is no blob rejection, a final check is made to see if the number of events forming the blob is sufficient to exceed a small defect threshold.

It is an object of the present invention to provide a means and apparatus for rapidly extracting significant data from a sparse object, such as a glass bottle.

It is another object of the present invention to provide a means and an apparatus to rapidly extract significant data from an object being inspected in a manner suitable for computer analysis.

It is a further object of the present invention to provide a sidewall inspection device that can be easily integrated with an existing apparatus for moving transparent or translucent items past an inspection point, thereby automating the inspection process.

Other objects and advantages of the invention will be apparent to those skilled in the art from the following detailed description of the preferred embodiment of the invention, when considered in light of the accompanying drawings.

DETAILED DESCRIPTION OF THE PREFERRED EMBODIMENTS

Figure 1:
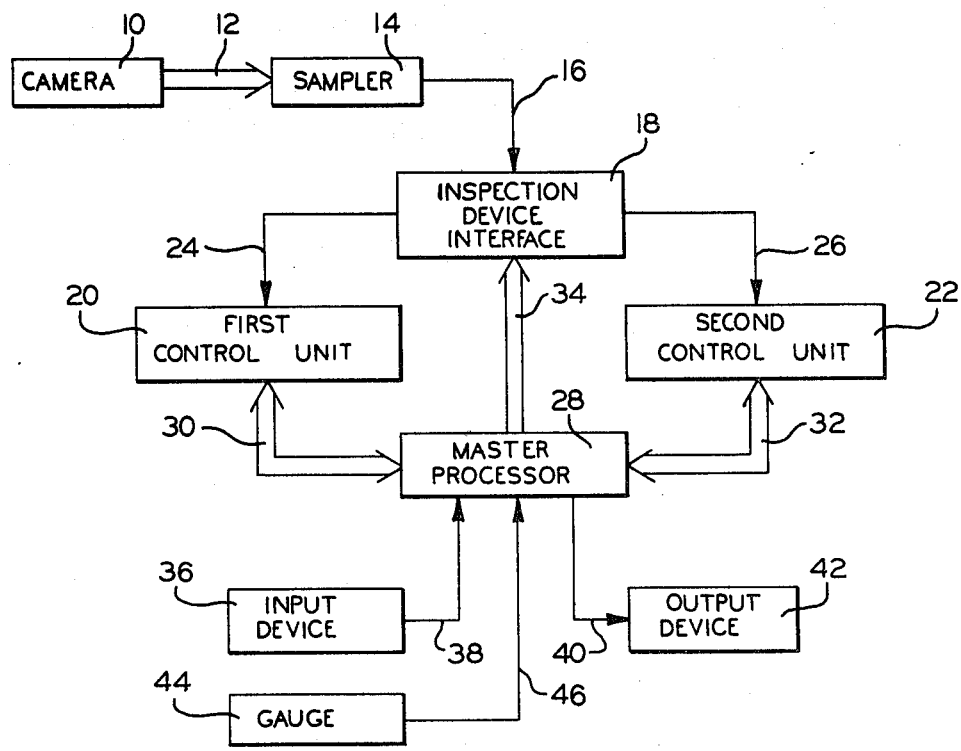
FIG. 1 is a block diagram of an apparatus for detecting defects in objects according to the present invention.

Referring now to the drawings, there is illustrated in FIG. 1 is a block diagram of an apparatus for detecting defects in objects according to the present invention. An object, such as a glass bottle (not shown), is scanned by a camera 10. The camera 10 generates a plurality of signals proportional in magnitude to the amount of light received from the glass bottle. In the preferred embodiment of the invention, a light source (not shown) directs a beam of light through the glass bottle under inspection and into the camera 10. The camera 10 includes a plurality of photosensitive devices, such as photodiodes, which are vertically arranged in a linear array. It has been found that a linear array of two hundred fifty-six photodiodes yields statisfactory results. The photodiode is a variable resistance device that will pass a voltage proportional to the amount of light falling thereon. Each photodiode receives light which has passed through different segments or portions of the bottle under inspection. If a flaw, crack, or foreign object is contained in the bottle, then the light passing through that portion of the bottle will be partially blocked or reflected and the corresponding photodiode will register a lesser intensity of light then had no defect been present.

The signals from the photodiodes of the camera 10 are supplied to a sampler 14 on a plurality of lines 12. Each of the photodiodes is sampled in sequential order, producing a series of pixel signals on a line 16 which represent the amount of light which passed through the bottle under inspection along one vertical sequential check or sweep of the photodiodes. The sampler 14 is a device well known in the art. By rotating the bottle under inspection relative to the camera 10, a plurality of different sweeps can be made, each sweep inspecting a different portion of the bottle. It has been found that about three hundred seventy-five to four hundred sweeps will sufficiently cover an average bottle and insure an accurate inspection. Thus, the sampler 14 generates a plurality of series of pixel signals on line 16 representing the amount of light passing through the inspected portions of the entire bottle.

The pixel signals from the sampler 14 on line 16 are an input to an inspection device interface 18. The interface 18 rapidly extracts significant data from a sparse object, such as a glass bottle, in a manner suitable for computer analysis. When a bottle is ready to be scanned, the interface 18 is enabled to receive and store data concerning that bottle. When no bottle is ready to be scanned, the interface 18 stores the data concerning the last scanned bottle until a new bottle is ready to be scanned. The operation of the interface 18 is more fully explained below.

The interface 18 is a means for generating groups of signals representing the characteristics of the bottle under inspection. The output of the interface 18 is fed to a control circuit for generating a reject signal whenever a defective bottle is detected. The control circuit includes a first control unit means 20 and a second control unit means 22, which receive the output signals from the interface 18 over lines 24 and 26 respectively. The first control unit 20 and the second control unit 22 are each responsive to the groups of signals representing the characteristics of the bottles under inspection for determining whether to generate a reject signal.

The first control unit 20 and the second control unit 22 are connected to a master control unit means or processor 28 by lines 30 and 32 respectively. The master processor 28 also provides inputs to the interface 18 over a plurality of lines 34 to allow an operator to set certain tolerance limits, as will be more fully described below. The master processor 28 alternatively connects one of the first and second control units 20 and 22 to the interface 18 to receive groups of signals representing the characteristics of a bottle while the other of the first and second control units 20 and 22 determines whether to generate a reject signal based upon the plurality of signals representing the characteristics of a preceding bottle. Thus, while the first control unit 20 is reading data from the inspection interface 18 concerning a bottle which has just been scanned, the second control unit 22 is processing data obtained on a prior scan to determine whether to generate a reject signal for the preceding bottle.

The master processor 28, the first control unit 20, and the second control unit 22 can all be microprocessors, such as a model 6800 manufactured by Motorola which is conventional and well known in the art. The master processor 28 has an input device 36 by which an operator can program the system and set various tolerance parameters. The input device 36 is connected to the master processor 28 by a line 38. The master processor 28 is also connected by a line 40 to an output device 42, such as a video display, so as to permit an operator to monitor or calibrate the system. Alternatively, the device 42 can be a means responsive to a reject signal generated by the master processor 28 for rejecting a particular bottle which has been determined to be defective. A further input to the master processor 28 is a gauge 44. The gauge 44 is provided to generate a signal on a line 46 when a bottle is in the proper position to be scanned.

The interface 18 can receive data so long as the gauge 44 signals that a bottle is in the proper scanning position. When the gauge 44 ceases to generate such a signal, as during the period when the inspected bottle is removed and an uninspected bottle is moved in, the collected information is stored in the interface 18. The master processor 28 prevents interference between the first and second control units 20 and 22 by selecting one of the units to receive the data held in the interface 18. When all of the data has been transferred to the first control unit 20, for example, the interface 18 is free to receive new data on the next bottle as soon as the signal from the gauge 44 is restored. The first control unit 20 processes the data in order to determine whether to generate a reject signal. When scanning is completed on the next bottle and the gauge 44 ceases to generate its signal, the accumulated data is stored in the interface 18. The master processor 28 then selects the second control unit 22 to receive the data while the first control unit 20 continues to process the original information. Thus, each of the control units 20 and 22 has two full cycles of the gauge 44 to process the data concerning each bottle to determine whether or not to generate a reject signal. By providing parallel processing paths, the control circuit increases the speed and efficiency of the inspection apparatus.

Figure 2:
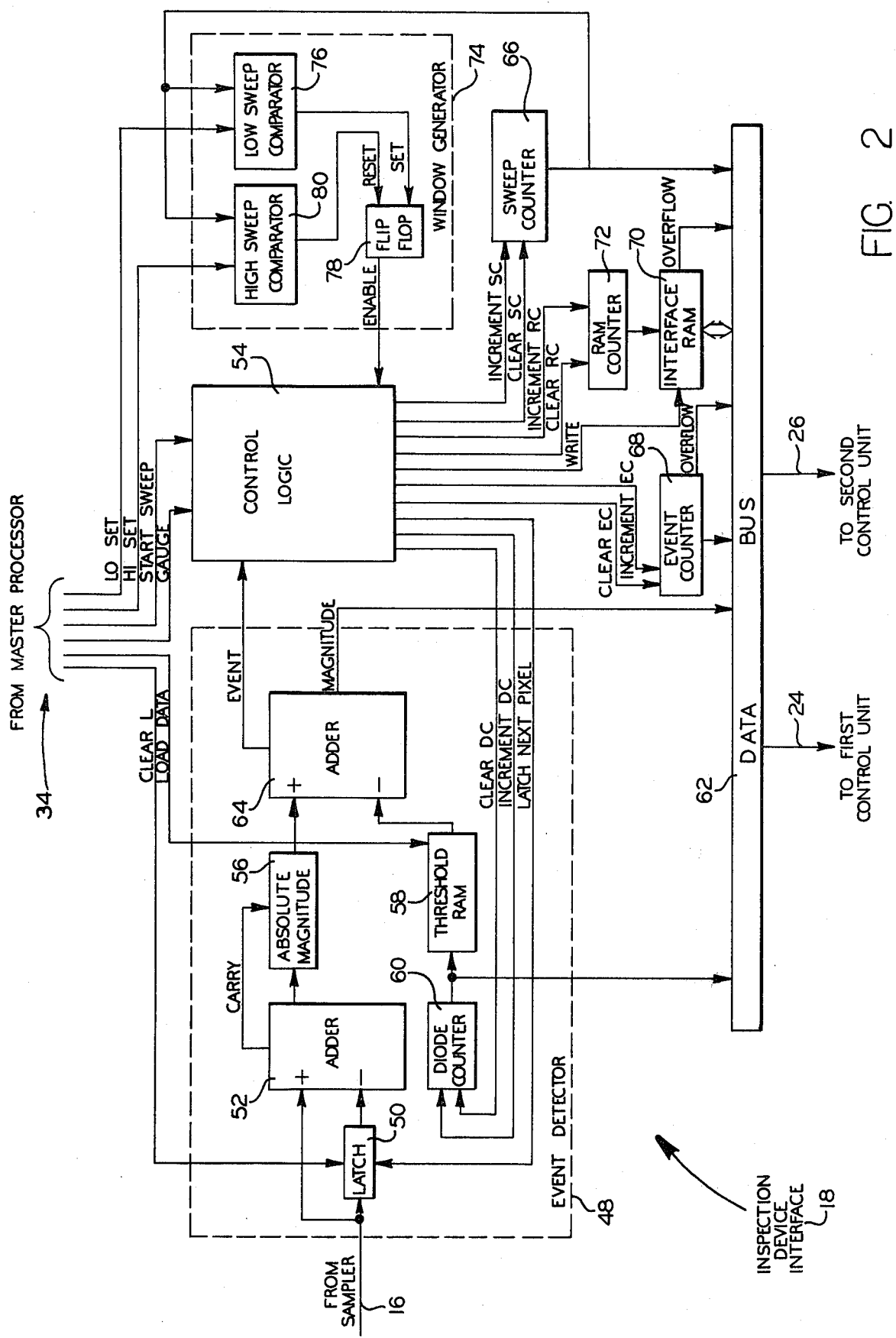
FIG. 2 is a block diagram of the inspection device interface of the apparatus for detecting defects of FIG. 1.

Referring now to FIG. 2, there is illustrated a block diagram of the details of the inspection device interface 18. The interface 18 is a means for rapidly extracting significant data from a sparse object, such as a glass bottle, in a manner suitable for computer analysis. The sampler 14 can generate digital signals, or analog signals to an analog-to-digital converter, representing the magnitude of the light received by the camera 10. Line 16 presents the plurality of signals to an event detector 48 including a data latch 50 and an adder 52. The latch is a means for storing one of the plurality of signals. In the illustrated embodiment, the preceding pixel signal is stored in the latch 50 and is presented to the complementary input of adder 52. Thus, the adder 52 is a means for generating a signal which represents the difference between the magnitude of the stored preceding pixel signal in the latch 50 and the successive pixel signal presented on line 16. The output of the adder 52 is a signal representing the difference in the magnitudes of adjacent pixel signals. When the difference signal is generated by adder 52, the present pixel signal is stored in latch 50 to be compared with the next pixel signal. A control logic unit 54 of the interface 18 generates a command over a LATCH NEXT PIXEL line to cause the latch 50 to store the present pixel signal available on line 16. The contents of the latch 50 can be cleared to zero by a command from the master processor 28 over a CLEAR L line.

The difference signal from the adder 52 can be either positive or negative, depending upon the magnitudes of the present and previous pixel signals. Because only the magnitude of the difference between adjacent pixel signals is relevant in the detection of defects, it is convenient to feed the difference signal to a means for generating the absolute magnitude of the difference signal. As illustrated, the output from adder 52 is fed to an absolute magnitude circuit 56. The circuit 56 can be constructed of a plurality of exclusive OR gates, as is well known in the art. The CARRY output of adder 52 controls the absolute magnitude circuit 56 such that the output is always positive. Rectification of the difference signal prevents misleading comparison readings in the event detector 48.

The event detector 48 includes a means for storing a threshold signal. In the preferred embodiment, a threshold random access memory (RAM) 58 is provided for storing a plurality of threshold signals. Each threshold signal stored in the threshold RAM 58 corresponds to a specific pixel difference signal generated by the adder 52. The means for selecting the individual threshold signal from the threshold RAM 58 which corresponds to the present difference signal is a diode counter 60. The diode counter 60 can be cleared to zero by a command from the control logic 54 over a CLEAR DC line and can be incremented by a command over an INCREMENT DC line. The diode counter 60 provides the threshold RAM 58 with the memory address of the proper threshold signal. The desired threshold signals can be loaded into the threshold RAM 58 from the master processor 28 over a LOAD DATA line. The output of the diode counter 60 is also connected to an internal data bus 62.

The signal from the threshold RAM 58 is presented to the complementary input of an adder 64 where it is combined with the signal from the absolute magnitude circuit 56. The adder 64 is a means for generating event signals when the difference signal obtained from the absolute magnitude circuit 56 exceeds the threshold signal obtained from the threshold RAM 58. Event signals are generated, over an EVENT line to the control logic 54, indicating the detection of a defect, and over a MAGNITUDE line to the internal data bus 62, indicating by how much the difference signal differed from the threshold signal.

Upon receiving a signal from the gauge 44 that a bottle is ready to be scanned, the master processor 28 generates a signal over a GAUGE line to the control logic 54. In response to that signal, the control logic 54 generates a signal over a CLEAR SC line to a sweep counter 66. The contents of the sweep counter 66 are thus cleared to zero before each bottle is scanned. The output of the sweep counter 66 is connected to the internal data bus 62.

To initiate a sweep, the master processor 28 generates a signal over a START SWEEP line to the control logic 54. In response to that signal, the control logic 54 increments the sweep counter 66 by generating a signal over an INCREMENT SC line. The control logic 54 also clears the contents of the diode counter by generating a signal over the CLEAR DC line. The control logic 54 further generates a signal over a CLEAR EC line to clear an event counter 68. These three initialization functions prepare the interface 18 for the receipt of data. The output of the event counter 68 is connected to the internal data bus 62. The event counter 68 generates a signal on an OVERFLOW line to the data bus 62 when the contents of the register exceed its limits. The event counter 68 is incremented by the control logic 54 over an INCREMENT EC line each time that the event detector 48 signals that an event has occurred.

The interface 18 includes a means for storing the event signals. An interface random access memory (RAM) 70 is provided for reading and storing the signals available on the data bus 62. The first control unit 20 and the second control unit 22 alternatively read the accumulated data from the interface RAM 70 through the data bus 62 and lines 24 and 26 respectively. Data is stored in the interface RAM 70 when the control logic 54 generates a signal over a WRITE line. The interface RAM 70 also generates a signal on an OVERFLOW line to the data bus 62 when the contents of the register exceed its limits. A RAM counter 72 provides the interface RAM 70 with memory address locations. The RAM counter 72 can be cleared to zero by a command from the control logic 54 over a CLEAR RC line and can be incremented by the control logic 54 by a command over an INCREMENT RC line.

The interface 18 also includes a means for defining a range for extracting data. In the illustrated embodiment, a window generator 74 is provided to limit the number of sweeps over which data can be extracted. A lower sweep limit is entered by an operator through the input device 36 to the master processor 28. The instruction is sent over a LO SET line to a low sweep comparator 76. The output of the sweep counter 66 is also an input to the low sweep comparator 76. When the number in the sweep counter 66 equals or exceeds the number generated over the LO SET line, the low sweep comparator 76 generates a signal over a SET line to a flip-flop 78. The flip-flop 78 generates a signal over an ENABLE line to the control logic 54, instructing it to process the incoming data. Signals received by the interface 18 on sweeps taken of a bottle below the lower sweep limit are ignored to prevent erroneous data associated with the initial sweeps from being processed. Similarly, the operator can enter a high sweep limit value to cause the interface 18 to stop processing data after a certain number of sweeps. The master processor 28 sends the instruction over a HI SET line to a high sweep comparator 80. The output of the sweep counter 66 is also an input to the high sweep comparator 80. When the number in the sweep counter 66 equals or exceeds the number generated over the HI SET line, the high sweep comparator 80 generates a signal over a RESET line to the flip-flop 78. The flip-flop 78 thus ceases to generate the signal over the ENABLE line, causing the control logic 54 to ignore all subsequent data.

Prior to utilizing the apparatus for detecting defects, the operator will enter the parameters under which the machine will operate through the input device 36. The parameters include the low and high sweep limits and the group of threshold signals. The low and high sweep limits define the sweep window, which is the range of sweeps over which data can be accepted by the interface 18. By selecting a particular set of threshold signals to be loaded into the threshold RAM 58, the operator determines the acceptable tolerances of light deviation which will cause an event to be detected. The master processor 28 loads the appropriate data into the interface 18.

When a bottle has been moved into a proper position for scanning, the gauge 44 generates a signal to the master processor 28. The signal is relayed along the GAUGE line to the control logic 54, which generates signals to clear the contents of both the sweep counter 66 and the RAM counter 72. These tasks are performed each time a new bottle is ready to be inspected. The interface 18 is then prepared to receive data from the camera 10.

At the beginning of each sweep, the master processor 28 generates a signal over the START SWEEP line to the control logic 54. The control logic 54 generates appropriate signals to clear the contents of the diode counter 60, clear the contents of the event counter 68, and increment the contents of the sweep counter 66. These tasks are performed at the beginning of each sweep made by the sampler 14.

The incoming pixel signals are fed to the adder 52 and the latch 50. The latch 50 holds the previous pixel signal at its output, which is then fed to the complementary input of the adder 52. Thus, the output of the adder 52 represents the difference between the two adjacent pixel signals. The output of the adder 52 is fed to the absolute magnitude circuit 56, which insures that the input to adder 64 is always a positive signal.

The threshold RAM 58 holds the programmed plurality of threshold signals, each of which corresponds to a specific difference signal representing a pair of pixels. Since each pixel signal represents a sampled photodiode in the camera 10, the diode counter 60 can be incremented with each incoming pixel signal to select the memory address of the appropriate threshold signal stored in the threshold RAM 58. That particular threshold signal is fed to the complementary input of adder 64 to be compared with the actual difference signal generated by adder 52 and rectified by the absolute magnitude circuit 56. The output of adder 64 is a plurality of event signals which represent a comparison between the difference signal and the threshold signal. When the magnitude of the difference signal exceeds the threshold signal, the adder 64 will generate an event signal over the EVENT line to the control logic 54. The magnitude of the event signal as well as the output of the diode counter are gated onto the data bus 62 for storage in the interface RAM 70.

When an event is detected during the sweep window, as defined by the operator using the window generator 74, the control logic 54 generates signals which increment the event counter 68 and increment the RAM counter 72. The control logic 54 also generates a signal over the WRITE line to the interface RAM 70 to read and store the contents of the diode counter 60 and the magnitude of the output adder 64. This process is repeated with each pair of adjacent pixel signals until a sweep is completed. The signal on the START SWEEP line is removed at the end of each sweep, causing the contents of the sweep counter 66 and the event counter 68 to be written into the interface RAM 70 if one or more events have occurred in that particular sweep. Thus, in each sweep where an event is detected, the gathered data includes a series of events denoted by diode number and event magnitude, followed by a final single entry consisting of the sweep number and the number of events which occurred in that sweep. When the next sweep of the same bottle begins, the contents of the diode counter 60 are cleared to zero, the contents of the event counter 68 are cleared to zero, and the sweep counter 66 is again incremented. The scanning continues until the window generator 74 disables the interface 18 when the high sweep limit has been reached.

The groups of signals stored in the interface RAM 70 which represent the characteristics of the inspected bottle are then fed to either the first control unit 20 or the second control unit 22, as determined by the master processor 28. The data in the interface RAM 70 is downloaded into the selected control unit, which determines whether or not to generate a reject signal for that particular bottle. Two checks are made before processing begins to make sure that the interface 18 has not overflowed because of an unusually bad bottle. These checks are indicated by status flags on the event counter 68 and the interface RAM 70. If the contents of either unit exceeds the capability of the register, a signal is generated over the respective OVERFLOW lines. When either overflow signal is present, the bottle will be immediately rejected because of a gross defect.

As stated above, the format of the data which is read by the selected control unit includes a series of diode numbers and associated event magnitudes, followed by a sweep number and a number of events. The bottle data is downloaded from the interface RAM 70 to the particular control unit. By checking each event along a sweep to see if it can be linked to a preceding event, the control units 20 or 22 can generate a string. A string is defined as a collection of one or more events in proximity to each other and having four properties which are calculated during generation. These properties include: the beginning of the string, which is the first diode number; the end of the string, which is the last diode number; the magnitude of each string, which is the sum of the magnitudes of each event comprising the string; and the number of events that formed the string. Checking for excess string magnitude occurs during string generation and the decision process will halt if a string magnitude exceeds a user-adjustable threshold. In other words, the selected control unit 20 or 22 links together events within a single sweep to determine if the sum of the magnitudes of the events exceeds a user-specified tolerance. If so, a reject signal is generated and the particular bottle will be removed.

If string checking does not reject the bottle, another processing stage is entered wherein the strings are checked to see if they form blobs. A blob is defined as collection of strings in proximity to each other. The string diode numbers must overlap, or at most be within a user-specified range, for the end of one string on one sweep and the beginning of another string on a different sweep. A blob has three properties which are calculated during formation. These properties include blob width, blob magnitude, and the number of events in the blob. During blob formation, blob width and blob magnitude are checked against user-specified tolerances and processing stops if either threshold is exceeded. If a bottle is not rejected because of blob width or blob magnitude, the number of events contained in the blob is compared to another user-specified number. If the number of events exceeds the specified tolerance, the bottle will also be rejected. If the bottle has not been rejected for any of the above reasons, it is considered a good bottle and no reject signal will be generated.

The apparatus for detecting defects can also be utilized to generate and display a picture of the object under inspection. A bottle is inspected under the normal procedure described above and data is stored in the interface RAM 70. When the bottle has been completely scanned, the master processor 28 instructs either the first control unit 20 or the second control unit 22 to receive the data from the inspection interface 18. The selected control unit 20 or 22 does not process the received information but rather transmits the data in raw form to the master processor 28. The gathered data includes the diode number, the sweep number, and the event magnitude for each event detected by the interface 18. The data is then presented to the output device 42, which can include a two-dimensional graphic module and a video screen. The graphic module and video screen are well known in the art. The data can be displayed in a two-dimensional graphic form, utilizing the sweep number of each event as the horizontal component and the diode number of each event as the vertical component. The video screen will display a dot at each sweep and diode number location where an event was detected. The result is a two-dimensional representation of the inspected bottle showing all of the detected defects, as if the bottle had been cut through one side and unwrapped for display. The event magnitude may be used in conjunction with a synthetic threshold level which can be varied to generate new pictures which show the effect that different threshold levels have. Using the apparatus in this mode, an operator is aided in determining what the appropriate threshold levels for the particular style of bottle should be. Although the preferred embodiment of the invention provides only a two-dimensional representation of the object under inspection, it will be appreciated that a three-dimensional representation could be generated on the video screen by the use of additional circuitry. Such circuitry is also well known in the art.

The apparatus for detecting defects can also be utilized to monitor the video output of the line scan camera. Such a use permits an operator to calibrate the interface 18 without requiring the use of an oscilloscope. When the apparatus is operated in this mode, the master processor 28 continuously clears the contents of the latch 50 to zero by generating a signal over the CLEAR L line. With the latch 50 cleared, the plurality of pixel signals on lines 16 from the sampler 14 pass through the adder 52 unaltered. The master processor 28 also utilizes the LOAD DATA line to load the threshold RAM 58 with all zeros. Thus, every pixel signal is detected as an event and is stored in the interface RAM 70. Since the interface RAM 70 is limited in size, only one sweep of the bottle is taken to prevent memory overflow. The master processor 28 selects either the first control unit 20 or the second control unit 22 to receive the data from the interface RAM 70. The data includes the diode number and event magnitude for each pixel of the sweep. The data is transferred from the selected control unit 20 or 22 to the master processor 28. The master processor 28 relays the information to the output device 42, which again can consist of a two-dimensional graphic module and a video screen. The graphic module can utilize the diode number as the horizontal component and the event magnitude as the vertical component. The graph which is thus displayed on the video screen represents the amount of light received by the photodiodes over a single sweep. The procedure can be repeated continuously to simulate an oscilloscope. However, unlike an oscilloscope, no sweep or gain adjustments are necessary since the data is always properly scaled to a specific diode number or event magnitude. Operation of the apparatus in this mode permits an operator to make sensitivity adjustments relating to the event magnitude voltage without requiring the use of an oscilloscope.

In accordance with the provisions of the patent statutes, the principle and mode of operation of the invention have been explained and illustrated in its preferred embodiment. However, it must be understood that the invention may be practiced otherwise than as specifically illustrated and described without departing from its spirit or scope.

What is claimed is:

1. An inspection device in an apparatus for detecting defects in successive objects and for providing a plurality of pixel signals each representing the magnitude of light received from a corresponding point on an object, said inspection device comprising:

an interface means responsive to the pixel signals for comparing successive adjacent pixel signals and generating an event signal when said comparison indicates the presence of a defect, said interface means storing a readable group of characteristic signals representing the total number of event signals generated by a corresponding object, each characteristic signal including a first signal indicating the magnitude of a corresponding event signal and a second signal indicating the location of the point on the object from which the event signal is generated; and first and second control means respectively responsive to successive groups of characteristic signals corresponding to successive objects for processing said characteristic signals and providing a reject signal to discard the corresponding object when one of said first and second control means indicates that a rejectable defect is present.

2. An inspection device as recited in claim 1 wherein said interface means compares successive adjacent pixel signals and generates an event signal when the absolute value of the difference between the magnitudes of the adjacent pixel signals exceeds a predetermined threshold value associated with the location of the corresponding point on the object.

3. An inspection device as recited in claim 2 wherein said interface means stores a magnitude characteristic signal having a value equal to the difference between said absolute value and said threshold value.

4. An inspection device as recited in claims 1 or 3 wherein the pixel signals are provided by a photodiode array having a plurality of photodiodes, each one providing one of the pixel signals, and wherein said interface means compares successive pixel signals from adjacent ones of the photodiodes.

5. An inspection device as recited in claims 1 or 3 wherein the pixel signals are provided by a photodiode array having a plurality of photodiodes, each providing one of the pixel signals, and wherein said location characteristic signals each represent the position of a photodiode in the photodiode array corresponding to the location of the point on the object from which the event signal is generated.

6. An inspection device as recited in claims 1 or 3 wherein said interface means includes a random access memory for storing said group characteristic signals.

7. An inspection device as recited in claims 1 or 3 wherein said interface means also stores a readable magnitude summation signal for each group of characteristic signals, said magnitude summation signal being equal to the sum of the magnitude characteristic signals generated by a corresponding object; and wherein said first and second control means are also responsive to the magnitude summation signal to provide a reject signal when said magnitude summation signal exceeds a predetermined value.

8. An inspection device as recited in claims 1 or 3 wherein said interface means also stores a readable event summation signal for each group of characteristic signals, said event summation signal being equal to the total number of event signals generated by a corresponding object; and wherein said first and second control means are responsive to said event summation signal to provide a reject signal when said event summation signal exceeds a predetermined value.

9. An inspection device as recited in claims 1 or 3 wherein the pixel signals are provided by a photodiode array having a plurality of photodiodes, each providing one of the pixel signals, and wherein said interface means compares successive pixel signals from adjacent ones of said photodiodes to generate a string of event signals; and wherein said first and second control means are responsive to said magnitude characteristic signals to calculate a string magnitude signal equal to the sum of the magnitude characteristic signals in said string and to provide a reject signal when said string magnitude signal exceeds a predetermined value.

10. An inspection device as recited in claim 9 wherein said interface means generates a plurality of said strings for an object; and wherein said first and second control means are responsive to said magnitude characteristic signals and said location characteristic signals among strings in proximity to each other to calculate a blob magnitude signal equal to the sum of the magnitude characteristic signals among said strings and to provide a reject signal when said blob magnitude signal exceeds a predetermined value.

11. An inspection device as recited in claim 9 wherein said interface means generates a plurality of said strings for an object; and wherein said first and second control means are responsive to said magnitude characteristic signals and said location characteristic signals among strings in proximity to each other to calculate a blob width signal equal to the number of magnitude characteristic signals among said strings and to provide a reject signal when said blob width signal exceeds a predetermined value.

12. An inspection device as recited in claim 9 wherein said interface means generates a plurality of said strings for an object; and wherein said first and second control means are responsive to said magnitude characteristic signals and said location characteristic signals among strings in proximity to each other to calculate a blob area signal equal to the total number of events among said strings and to provide a reject signal when said blob area signal exceeds a predetermined value.

13. An inspection device in an apparatus for detecting defects in successive objects and for providing a plurality of pixel signals each representing the magnitude of light received from a corresponding point on an object, said inspection device comprising:
an interface means responsive to successive adjacent pixel signals for generating an event signal when the absolute-value of the difference between the magnitude of adjacent pixel signals exceeds a predetermined threshold value associated with the location of a corresponding point on the object, said interface means storing a readable group of characteristic signals representing the total number of event signals generated by a corresponding object, each characteristic signal including a first signal indicating the magnitude of the corresponding events signal and a second signal indicating the location of the point on the object from which the event signal is generated; and
first and second control means respectively responsive to successive groups of characteristic signals corresponding to successive objects for processing said characteristic signals and providing a reject signal to discard the corresponding object when one of said first and second control means indicates that a rejectable defect is present.

14. An inspection device as recited in claim 13 wherein the pixel signals are provided in a serial format and wherein said interface means comprises means for latching one of said pixel signals, first means responsive to said latching means for comparing one of said pixel signals with a preceding one of said pixel signals in said latching means to provide a difference signal equal to the difference in magnitudes of said pixel signals, means responsive to said first comparing means for providing the absolute-value of said difference signal, means for storing a plurality of threshold signals, and second means responsive to said absolute-value means and said threshold storage means for comparing the absolute-value of each of said difference signals to a correspondingly stored threshold signal to generate one of said event signals when the absolute value of the magnitude of said difference signal exceeds the magnitude of said corresponding threshold signal.

15. An inspection device as recited in claim 14 wherein said interface means further comprises means responsive to said second comparing means for storing a magnitude characteristic signal having a value equal to the difference between said absolute value and said threshold value.

16. An inspection device as recited in claims 14 or 15 wherein said interface means further comprises means responsive to said second comparing means for storing a magnitude summation signal equal to the sum of the magnitude characteristic signals generated by a corresponding object.

17. An inspection device as recited in claim 14 wherein said interface means further comprises means responsive to said second comparing means for storing an event summation signal equal to the total number of event signals generated by a corresponding object.

18. An inspection device as recited in claim 14 wherein the pixel signals are provided by a photodiode array having a plurality of photodiodes, each one providing one of the pixel signals, and wherein said interface means is responsive to successive pixel signals from adjacent ones of the photodiodes to generate a string of event signals.

19. An inspection device as recited in claim 18 wherein said threshold storing means includes a random access memory for storing a string of threshold values for comparison to a corresponding string of absolute-value signals representing the absolute value of the difference between the magnitude of adjacent pixel signals provided by adjacent photodiodes.

20. An inspection device as recited in claim 19 wherein said interface means further comprises means for selecting one of said threshold values associated with a corresponding one of said absolute-value signals.

21. An inspection device as recited in claim 20 wherein said interface means further comprises means for counting the number of said strings of event signals and means for storing a location characteristic signal having a value determined by said threshold selection means and said string counting means.

22. An inspection device as recited in claim 21 wherein said interface means further comprises maximum string means responsive to said string counting means for limiting an allowable number of strings of event signals for each object.

23. An inspection device in an apparatus for detecting defects in successive objects and for providing a plurality of pixel signals each representing the magnitude of light received from a corresponding point on an object, said inspection device comprising:

an interface means responsive to the pixel signals for comparing successive adjacent pixel signals and generating an event signal when said comparison indicates the presence of a defect, said interface means storing a readable group of characteristic signals representing the total number of event signals generated by a corresponding object, each characteristic signal including a first signal indicating the magnitude of a corresponding event signal and a second signal indicating the location of the point on the object from which the event signal is generated;

first and second control means respectively responsive to successive groups of characteristic signals corresponding to successive objects for processing said characteristic signals and providing a reject signal to discard the corresponding object when one of said first and second control means indicates that a rejectable defect is present; and a master control means connected to said first and second control means for alternately connecting one of said first and second control means to said interface means so that one reads a group of said characteristic signals for one object while the other processes a group of said characteristic signals for a preceding object.

24. An inspection device as recited in claims 23 wherein said interface means compares successive adjacent pixel signals and generates an event signal when the absolute value of the difference between the magnitudes of the adjacent pixel signals exceeds a predetermined threshold value associated with the location of the corresponding point on the object.

25. An inspection device as recited in claim 24 wherein said interface means stores a magnitude characteristic signal having a value equal to the difference between said absolute value and said threshold value.

26. A method for detecting defects in an object being inspected by an apparatus providing a plurality of pixel signals each representing the magnitude of light received from a corresponding point on an object, comprising the steps of:

(a) generating an event signal when the absolute value of the difference between the magnitudes of adjacent pixel signals exceeds a predetermined threshold value associated with the location of a corresponding point on the object indicating the presence of a defect at that point;

(b) storing a readable group of characteristic signals representing the total number of event signals generated by a corresponding object, each characteristic signal including a first signal indicating the magnitude of a corresponding event signal and a second signal indicating the location of the point on the object from which the event signal is generated;

(c) processing a group of characteristic signals to identify the presence of a defect in a corresponding object; and (d) providing a reject signal to discard the object when a rejectable defect is identified.

27. A method as recited in claim 26 further comprising a step of reading a group of characteristic signals for one object while step (c) is processing a group of characteristic signals for a preceding object.

28. A method as recited in claims 26 or 27 wherein step (b) also stores a readable magnitude summation signal for each group of characteristic signals, the magnitude summation signal being equal to the sum of the magnitude characteristic signals generated by a corresponding object, and step (c) identifies the presence of a defect when the magnitude summation signal exceeds a predetermined value.

29. A method as recited in claims 26 or 27 wherein step (b) also stores a readable event summation signal for each group of characteristic signals, the event summation signal being equal to the total number of event signals generated by a corresponding object, and step (c) identifies the presence of a defect when the event summation signal exceeds a predetermined value.

30. A method as recited in claims 26 or 27 wherein the pixel signals are provided by a photodiode array having a plurality of photodiodes, each providing one of the pixel signals, and wherein step (a) generates a string of event signals for the photodiode array and step (c) identifies the presence of a defect when the sum of the magnitude characteristic signals in the string exceeds a predetermined value.

31. A method as recited in claim 30 wherein step (a) generates a plurality of strings for an object and step (c) identifies the presence of a defect when the sum of the magnitude characteristic signals among strings in proximity to each other exceeds a predetermined value.

32. A method as recited in claim 30 wherein step (a) generates a plurality of strings for an object and step (c) identifies the presence of a defect when the number of magnitude characteristic signals among strings in proximity to each other exceeds a predetermined value.

* * * * *